United States Patent [19]

Blattner

[11] Patent Number: 5,227,288
[45] Date of Patent: Jul. 13, 1993

[54] DNA SEQUENCING VECTOR WITH REVERSIBLE INSERT

[76] Inventor: Frederick R. Blattner, 1547 Jefferson St., Madison, Wis. 53711

[21] Appl. No.: 590,988

[22] Filed: Oct. 1, 1990

[51] Int. Cl.$^5$ .................... C12Q 1/68; C12N 15/00
[52] U.S. Cl. .................... 435/6; 435/252.3; 435/252.33; 435/320.1; 935/29; 935/72; 935/73
[58] Field of Search .............. 435/6, 91, 320.1, 252.3, 435/252.33, 172.3; 935/29, 31, 72, 73, 77

[56] References Cited

U.S. PATENT DOCUMENTS 4,673,640  6/1987  Backman ........................... 435/69.1

OTHER PUBLICATIONS

Daniels et al., *Lambda II*, Weisburg et al., Ed., Appendix 2, pp. 519-576 (1983).
Hasan et al., *Gene*, 56:1, pp. 145-151 (1987) (Abstract only).
Hsu et al., *Nature*, 285 pp. 85-91 (1980).
Lee et al., *J. Bacteriol.*, 172:3, pp. 1529-1538 (1990).
Mizuuchi et al., *Nucleic Acids Research*, 13:4, pp. 1193-1208 (1985).
Schroeder et al., *Nucleic Acids Research*, 10:1, pp. 69-84 (1982).
Yanisch-Perron et al., *Gene*, 33, pp. 103-119 (1985).

*Primary Examiner*—James Martinell
*Attorney, Agent, or Firm*—Quarles & Brady

[57] ABSTRACT

A sequencing vector based on the M13 phage vector is disclosed which is particularly adapted for use in large scale DNA sequencing procedures. The vector includes a vector unique restriction site flanked by recognition sites, attP and attB, for the site specific recombination as catalyzed by a site specific recombination agent, lambda integrase. Using the vector, which incorporates the capability from M13 to replicate single stranded DNA for dideoxynucleotide sequencing, single stranded DNA of either strand may be selectively created since the orientation of any insert into the restriction site can readily be reversed by exposure of the vector to the recombination agent. This capability is particularly useful in large scale semi-random DNA sequencing in which the ability to selectively produce opposite strands is useful in filling gaps or ambiguities in large sequences.

26 Claims, 5 Drawing Sheets

FIG. 1

The sequence of JANUS

```
    1 AATGCTACTACTATTAGTAGAATTGATGCCACCTTTTCAGCTCGCGCCCC    50
   51 AAATGAAAATATAGCTAAACAGGTTATTGACCATTTGCGAAATGTATCTA   100
  101 ATGGTCAAACTAAATCTACTCGTTCGCAGAATTGGGAATCAACTGTTACA   150
  151 TGGAATGAAACTTCCAGACACCGTACTTTAGTTGCATATTTAAAACATGT   200
  201 TGAGCTACAGCACCAGATTCAGCAATTAAGCTCTAAGCCATCCGCAAAAA   250
  251 TGACCTCTTATCAAAAGGAGCAATTAAAGGTACTCTCTAATCCTGACCTG   300
  301 TTGGAGTTTGCTTCCGGTCTGGTTCGCTTTGAAGCTCGAATTAAAACGCG   350
  351 ATATTTGAAGTCTTTCGGGCTTCCTCTTAATCTTTTGATGCAATCCGCT   400
  401 TTGCTTCTGACTATAATAGTCAGGGTAAAGACCTGATTTTTGATTTATGG   450
  451 TCATTCTCGTTTTCTGAACTGTTTAAAGCATTTGAGGGGATTCAATGAA   500
  501 TATTTATGACGATTCCGCAGTATTGGACGCTATCCAGTCTAAACATTTTA   550
  551 CTATTACCCCCTCTGGCAAAACTTCTTTTGCAAAAGCCTCTCGCTATTTT   600
  601 GGTTTTTATCGTCGTCTGGTAAACGAGGGTTATGATAGTGTTGCTCTTAC   650
  651 TATGCCTCGTAATTCCTTTTGGCGTTATGTATCTGCATTAGTTGAATGTG   700
  701 GTATTCCTAAATCTCAACTGATGAATCTTTCTACCTGTAATAATGTTGTT   750
  751 CCGTTAGTTCGTTTTATTAACGTAGATTTTTCTTCCCAACGTCCTGACTG   800
  801 GTATAATGAGCCAGTTCTTAAAATCGCATAAGGTAATTCACAATGATTAA   850
  851 AGTTGAAATTAAACCATCTCAAGCCCAATTTACTACTCGTTCTGGTGTTC   900
  901 TCGTCAGGGCAAGCCTTATTCACTGAATGAGCAGCTTTGTTACGTTGATT   950
  951 TGGGTAATGAATATCCGGTTCTTGTCAAGATTACTCTTGATGAAGGTCAG  1000
 1001 CCAGCCTATGCGCCTGGTCTGTACACCGTTCATCTGTCCTCTTTCAAAGT  1050
 1051 TGGTCAGTTCGGTTCCCTTATGATTGACCGTCTGCGCCTCGTTCCGGCTA  1100
 1101 AGTAACATGGAGCAGGTCGCGGATTTCGACACAATTTATCAGGCGATGAT  1150
 1151 ACAAATCTCCGTTGTACTTTGTTTCGCGCTTGGTATAATCGCTGGGGGTC  1200
 1201 AAAGATGAGTGTTTTAGTGTATTCTTTCGCCTCTTTCGTTTTAGGTTGGT  1250
 1251 GCCTTCGTAGTGGCATTACGTATTTTACCCGTTTAATGGAAACTTCCTCA  1300
 1301 TGAAAAGTCTTTAGTCCTCAAAGCCTCTGTAGCCGTTGCTACCCTCGTT  1350
 1351 CCGATGCTGTCTTTCGCTGCTGAGGGTGACGATCCCGCAAAAGCGGCCTT  1400
 1401 TAACTCCCTGCAAGCCTCAGCGACCGAATATATCGGTTATGCGTGGGCGA  1450
 1451 TGGTTGTTGTCATTGTCGGCGCAACTATCGGTATCAAGCTGTTTAAGAAA  1500
 1501 TTCACCTCGAAAGCAAGCTGATAAACCGATACAATTAAAGGCTCCTTTTG  1550
 1551 GAGCCTTTTTTTTTGGAGATTTTCAACGTGAAAAAATTATTATTCGCAAT  1600
 1601 TCCTTTAGTTGTTCCTTTCTATTCTCACTCCGCTGAAACTGTTGAAAGTT  1650
 1651 GTTTAGCAAAACCCCATACAGAAAATTCATTTACTAACGTCTGGAAAGAC  1700
 1701 GACAAAACTTTAGATCGTTACGCTAACTATGAGGGTTGTCTGTGGAATGC  1750
 1751 TACAGGCGTTGTAGTTTGTACTGGTGACGAAACTCAGTGTTACGGTACAT  1800
 1801 GGGTTCCTATTGGGCTTGCTATCCCTGAAAATGAGGGTGGTGGCTCTGAG  1850
 1851 GGTGGCGGTTCTGAGGGTGGCGGTTCTGAGGGTGGCGGTACTAAACCTCC  1900
 1901 TGAGTACGGTGATACACCTATTCCGGGCTATACTTATATCAACCCTCTCG  1950
 1951 ACGGCACTTATCCGCCTGGTACTGAGCAAAACCCCGCTAATCCTAATCCT  2000
 2001 TCTCTTGAGGAGTCTCAGCCTCTTAATACTTTCATGTTTCAGAATAATAG  2050
 2051 GTTCCGAAATAGGCAGGGGGCATTAACTGTTTATACGGGCACTGTTACTC  2100
```

FIG. 2A

```
2101 AAGGCACTGACCCCGTTAAAACTTATTACCAGTACACTCCTGTATCATCA 2150
2151 AAAGCCATGTATGACGCTTACTGGAACGGTAAATTCAGAGACTGCGCTTT 2200
2201 CCATTCTGGCTTTAATGAAGATCCATTCGTTTGTGAATATCAAGGCCAAT 2250
     ----,----+----,----+----,----+----,----+----,----+
2251 CGTCTGACCTGCCTCAACCTCCTGTCAATGCTGGCGGCGGCTCTGGTGGT 2300
2301 GGTTCTGGTGGCGGCTCTGAGGGTGGTGGCTCTGAGGGTGGCGGTTCTGA 2350
2351 GGGTGGCGGCTCTGAGGGAGGCGGTTCCGGTGGTGGCTCTGGTTCCGGTG 2400
2401 ATTTTGATTATGAAAAGATGGCAAACGCTAATAAGGGGCTATGACCGAA 2450
2451 AATGCCGATGAAAACGCGCTACAGTCTGACGCTAAAGGCAAACTTGATTC 2500
     ----,----+----,----+----,----+----,----+----,----+
2501 TGTCGCTACTGATTACGGTGCTGCTATCGATGGTTTCATTGGTGACGTTT 2550
2551 CCGGCCTTGCTAATGGTAATGGTGCTACTGGTGATTTTGCTGGCTCTAAT 2600
2601 TCCCAAATGGCTCAAGTCGGTGACGGTGATAATTCACCTTTAATGAATAA 2650
2651 TTTCCGTCAATATTTACCTTCCCTCCCTCAATCGGTTGAATGTCGCCCTT 2700
2701 TTGTCTTTAGCGCTGGTAAACCATATGAATTTTCTATTGATTGTGACAAA 2750
     ----,----+----,----+----,----+----,----+----,----+
2751 ATAAACTTATTCCGTGGTGTCTTTGCGTTTCTTTTATATGTTGCCACCTT 2800
2801 TATGTATGTATTTTCTACGTTTGCTAACATACTGCGTAATAAGGAGTCTT 2850
2851 AATCATGCCAGTTCTTTTGGGTATTCCGTTATTATTGCGTTTCCTCGGTT 2900
2901 TCCTTCTGGTAACTTTGTTCGGCTATCTGCTTACTTTTCTTAAAAAGGGC 2950
2951 TTCGGTAAGATAGCTATTGCTATTTCATTGTTTCTTGCTCTTATTATTGG 3000
     ----,----+----,----+----,----+----,----+----,----+
3001 GCTTAACTCAATTCTTGTGGGTTATCTCTCTGATATTAGCGCTCAATTAC 3050
3051 CCTCTGACTTTGTTCAGGGTGTTCAGTTAATTCTCCCGTCTAATGCGCTT 3100
3101 CCCTGTTTTTATGTTATTCTCTCTGTAAAGGCTGCTATTTTCATTTTTGA 3150
3151 CGTTAAACAAAAAATCGTTTCTTATTTGGATTGGGATAAATAATATGGCT 3200
3201 GTTTATTTTGTAACTGGCAAATTAGGCTCTGGAAAGACGCTCGTTAGCGT 3250
     ----,----+----,----+----,----+----,----+----,----+
3251 TGGTAAGATTCAGGATAAAATTGTAGCTGGGTGCAAAATAGCAACTAATC 3300
3301 TTGATTTAAGGCTTCAAAACCTCCCGCAAGTCGGGAGGTTCGCTAAAACG 3350
3351 CCTCGCGTTCTTAGAATACCGGATAAGCCTTCTATATCTGATTTGCTTGC 3400
3401 TATTGGGCGCGGTAATGATTCCTACGATGAAAATAAAAACGGCTTGCTTG 3450
3451 TTCTCGATGAGTGCGGTACTTGGTTTAATACCCGTTCTTGGAATGATAAG 3500
     ----,----+----,----+----,----+----,----+----,----+
3501 GAAAGACAGCCGATTATTGATTGGTTTCTACATGCTCGTAAATTAGGATG 3550
3551 GGATATTATTTTTCTTGTTCAGGACTTATCTATTGTTGATAAACAGGCGC 3600
3601 GTTCTGCATTAGCTGAACATGTTGTTTATTGTCGTCGTCTGGACAGAATT 3650
3651 ACTTTACCTTTTGTCGGTACTTTATATTCTCTTATTACTGGCTCGAAAAT 3700
3701 GCCTCTGCCTAAATTACATGTTGGCGTTGTTAAATATGGCGATTCTCAAT 3750
     ----,----+----,----+----,----+----,----+----,----+
3751 TAAGCCCTACTGTTGAGCGTTGGCTTTATACTGGTAAGAATTTGTATAAC 3800
3801 GCATATGATACTAAACAGGCTTTTTCTAGTAATTATGATTCCGGTGTTTA 3850
3851 TTCTTATTTAACGCCTTATTTATCACACGGTCGGTATTTCAAACCATTAA 3900
3901 ATTTAGGTCAGAAGATGAAATTAACTAAAATATATTTGAAAAAGTTTTCT 3950
3951 CGCGTTCTTTGTCTTGCGATTGGATTTGCATCAGCATTTACATATAGTTA 4000
     ----,----+----,----+----,----+----,----+----,----+
4001 TATAACCCAACCTAAGCCGGAGGTTAAAAAGGTAGTCTCTCAGACCTATG 4050
4051 ATTTTGATAAATTCACTATTGACTCTTCTCAGCGTCTTAATCTAAGCTAT 4100
4101 CGCTATGTTTTCAAGGATTCTAAGGGAAAATTAATTAATAGCGACGATTT 4150
4151 ACAGAAGCAAGGTTATTCACTCACATATATTGATTTATGTACTGTTTCCA 4200
4201 TTAAAAAAGGTAATTCAAATGAAATTGTTAAATGTAATTAATTTTGTTTT 4250
     ----,----+----,----+----,----+----,----+----,----+
4251 CTTGATGTTTGTTTCATCATCTTCTTTTGCTCAGGTAATTGAAATGAATA 4300
4301 ATTCGCCTCTGCGCGATTTTGTAACTTGGTATTCAAAGCAATCAGGCGAA 4350
4351 TCCGTTATTGTTTCTCCCGATGTAAAAGGTACTGTTACTGTATATTCATC 4400
```

FIG. 2B

```
4401 TGACGTTAAACCTGAAAATCTACGCAATTTCTTTATTTCTGTTTTACGTG 4450
4451 CTAATAATTTGATATGGTTGGTTCAATTCCTTCCATAATTCAGAAGTAT 4500
     ----,----+----,----+----,----+----,----+----,----+
4501 AATCCAAACAATCAGGATTATATTGATGAATTGCCATCATCTGATAATCA 4550
4551 GGAATATGATGATAATTCCGCTCCTTCTGGTGGTTTCTTTGTTCCGCAAA 4600
4601 ATGATAATGTTACTCAAACTTTTAAAATTAATAACGTTCGGGCAAAGGAT 4650
4651 TTAATACGAGTTGTCGAATTGTTTGTAAAGTCTAATACTTCTAAATCCTC 4700
4701 AAATGTATTATCTATTGACGGCTCTAATCTATTAGTTGTTAGTGCACCTA 4750
     ----,----+----,----+----,----+----,----+----,----+
4751 AAGATATTTTAGATAACCTTCCTCAATTCCTTTCTACTGTTGATTTGCCA 4800
4801 ACTGACCAGATATTGATTGAGGGTTTGATATTTGAGGTTCAGCAAGGTGA 4850
4851 TGCTTTAGATTTTTCATTTGCTGCTGGCTCTCAGCGTGGCACTGTTGCAG 4900
4901 GCGGTGTTAATACTGACCGCCTCACCTCTGTTTTATCTTCTGCTGGTGGT 4950
4951 TCGTTCGGTATTTTTAATGGCGATGTTTTAGGGCTATCAGTTCGCGCATT 5000
     ----,----+----,----+----,----+----,----+----,----+
5001 AAAGACTAATAGCCATTCAAAATATTGTCTGTGCCACGTATTCTTACGC 5050
5051 TTTCAGGTCAGAAGGGTTCTATCTCTGTTGGCCAGAATGTCCCTTTTATT 5100
5101 ACTGGTCGTGTGACTGGTGAATCTGCCAATGTAAATAATCCATTTCAGAC 5150
5151 GATTGAGCGTCAAAATGTAGGTATTTCCATGAGCGTTTTTCCTGTTGCAA 5200
5201 TGGCTGGCGGTAATATTGTTCTGGATATTACCAGCAAGGCCGATAGTTTG 5250
     ----,----+----,----+----,----+----,----+----,----+
5251 AGTTCTTCTACTCAGGCAAGTGATGTTATTACTAATCAAAGAAGTATTGC 5300
5301 TACAACGGTTAATTTGCGTGATGGACAGACTCTTTTACTCGGTGGCCTCA 5350
5351 CTGATTATAAAAACACTTCTCAAGATTCTGGCGTACCGTTCCTGTCTAAA 5400
5401 ATCCCTTTAATCGGCCTCCTGTTTAGCTCCCGCTCTGATTCCAACGAGGA 5450
5451 AAGCACGTTATACGTGCTCGTCAAAGCAACCATAGTACGCGCCCTGTAGC 5500
     ----,----+----,----+----,----+----,----+----,----+
5501 GGCGCATTAAGCGCGGCGGGTGTGGTGGTTACGCGCAGCGTGACCGCTAC 5550
5551 ACTTGCCAGCGCCCTAGCGCCCGCTCCTTTCGCTTTCTTCCCTTCCTTTC 5600
5601 TCGCCACGTTCGCCGGCTTTCCCCGTCAAGCTCTAAATCGGGGGCTCCCT 5650
5651 TTAGGGTTCCGATTTAGTGCTTTACGGCACCTCGACCCCAAAAAACTTGA 5700
5701 TTTGGGTGATGGTTCACGTAGTGGGCCATCGCCCTGATAGACGGTTTTTC 5750
     ----,----+----,----+----,----+----,----+----,----+
5751 GCCCTTTGACGTTGGAGTCCACGTTCTTTAATAGTGGACTCTTGTTCCAA 5800
5801 ACTGGAACAACACTCAACCCTATCTCGGGCTATTCTTTTGATTTATAAGG 5850
5851 GATTTTGCCGATTTCGGAACCACCATCAAACAGGATTTTCGCCTGCTGGG 5900
5901 GCAAACCAGCGTGGACACGTTGGCGCTAATGCTCTGTTACAGGTCACTAA 5950
5951 TACCATCTAAGTAGTTGATTCATAGTGACTGCATATGTTGTGTTTACAG 6000
     ----,----+----,----+----,----+----,----+----,----+
6001 TATTATGTAGTCTGTTTTTTATGCAAAATCTAATTTAATATATTGATATT 6050
6051 TATATCATTTTACGTTTCTCGTTCAGCTTTTTTATACTAAGTTGGCATTA 6100
6101 TAAAAAAGCATTGCTTATCAATTTGTTGCAACGAACAGGTCACTATCAGT 6150
6151 CAAAATAAAATCATTATTTGATTTCAATTTTGTCCCACTCCCTGCCTCTG 6200
6201 TCATCACGATACTGTGATGCCATGGTGTCCGACTTATGCCCGAGAAGATG 6250
     ----,----+----,----+----,----+----,----+----,----+
6251 TTGAGCAAACTTATCGCTTATCTGCTTCTCATAGAGTCTTGCAGACAAAC 6300
6301 TGCGCAACTCGTGAAAGGTAGGCGGATCGACCGCTTGCTGCAACTCTCTC 6350
6351 AGGGCCAGGCGGTGAAGGGCAATCAGCTGTTGCCCGTCTCACTGGTGAAA 6400
6401 AGAAAAACCACCCTGGCGCCCAATACGCAAACCGCCTCTCCCCGCGCGTT 6450
6451 GGCCGATTCATTAATGCAGCTGGCACGACAGGTTTCCCGACTGGAAAGCG 6500
     ----,----+----,----+----,----+----,----+----,----+
6501 GGCAGTGAGCGCAACGCAATTAATGTGAGTTAGCTCACTCATTAGGCACC 6550
6551 CCAGGCTTTACACTTTATGCTTCCGGCTCGTATGTTGTGTGGAATTGTGA 6600
6601 GCGGATAACAATTTCACACAGGAAACAGCTATGACCATGATTACGCCAAG 6650
6651 CTCCCGGGGTCAAGTTAGTATAAAAAAGCAGGCATGGAATTCACTGGCCG 6700
```

FIG. 2C

```
6701  TCGTTTTACAACGTCGTGACTGGGAAAACCCTGGCGTTACCCAACTTAAT  6750
      ----,----+----,----+----,----+----,----+----,----+
6751  CGCCTTGCAGCACATCCCCCTTTCGCCAGCTGGCGTAATAGCGAAGAGGC  6800
6801  CCGCACCGATCGCCCTTCCCAACAGTTGCGCAGCCTGAATGGCGAATGGC  6850
6851  GCTTTGCCTGGTTTCCGGCACCAGAAGCGGTGCCGGAAAGCTGGCTGGAG  6900
6901  TGCGATCTTCCTGAGGCCGATACGGTCGTCGTCCCCTCAAACTGGCAGAT  6950
6951  GCACGGTTACGATGCGCCCATCTACACCAACGTAACCTATCCCATTACGG  7000
      ----,----+----,----+----,----+----,----+----,----+
7001  TCAATCCGCCGTTTGTTCCCACGGAGAATCCGACGGGTTGTTACTCGCTC  7050
7051  ACATTTAATGTTGATGAAAGCTGGCTACAGGAAGGCCAGACGCGAATTAT  7100
7101  TTTTGATGGCGTTCCTATTGGTTAAAAAATGAGCTGATTTAACAAAAATT  7150
7151  TAACGCGAATTTTAACAAAATATTAACGTTTACAATTTAAATATTTGCTT  7200
7201  ATACAATCTTCCTGTTTTTGGGGCTTTTCTGATTATCAACCGGGGTACAT  7250
      ----,----+----,----+----,----+----,----+----,----+
7251  ATGATTGACATGCTAGTTTTACGATTACCGTTCATCGATTCTCTTGTTTG  7300
7301  CTCCAGACTCTCAGGCAATGACCTGATAGCCTTTGTAGATCTCTCAAAAA  7350
7351  TAGCTACCCTCTCCGGCATTAATTTATCAGCTAGAACGGTTGAATATCAT  7400
7401  ATTGATGGTGATTTGACTGTCTCCGGCCTTTCTCACCCTTTTGAATCTTT  7450
7451  ACCTACACATTACTCAGGCATTGCATTTAAAATATATGAGGGTTCTAAAA  7500
      ----,----+----,----+----,----+----,----+----,----+
7501  ATTTTTATCCTTGCGTTGAAATAAAGGCTTCTCCCGCAAAAGTATTACAG  7550
7551  GGTCATAATGTTTTTGGTACAACCGATTTAGCTTTATGCTCTGAGGCTTT  7600
7601  ATTGCTTAATTTTGCTAATTCTTTGCCTTGCCTGTATGATTTATTGGATG  7650
7651  TT                                                  7652
```

FIG. 2D

DNA SEQUENCING VECTOR WITH REVERSIBLE INSERT

FIELD OF THE INVENTION

The present invention is generally directed toward the field of DNA vectors and is directed, in particular, to a DNA vector for particular use in nucleotide sequencing procedures.

BACKGROUND OF THE INVENTION

In the modern field of recombinant DNA technology, DNA strands are conventionally manipulated and reproduced by being inserted into larger pieces of DNA referred to as vectors. Such vectors serve as carrying vehicles both to transport the desired DNA from host to host, and to facilitate making multiple copies of DNA, i.e. clones, for various biological or analytical procedures.

One of the common objectives of modern biology is to determine the sequence of nucleotides in large DNA segments or genes. DNA sequencing technology is evolving to a point wherein it is being considered that efforts are being undertaken to determine the genetic code, or DNA sequence, of entire organisms. Such efforts are large in scale, even for relatively uncomplex organisms, and are massive in scale if considered for complex organisms such as vertebrates. The scale of such efforts mandates consideration of all possibilities of increasing the efficiency of DNA sequencing techniques.

Several techniques have been developed, therefore, to perform the actual base-to-base DNA sequencing. One commonly used method of DNA sequencing is referred to as dideoxynucleotide sequencing. In accordance with this technique, a single strand of DNA is sequenced through the use of a polymerase which elongates a complementary DNA strand from a radiolabelled primer along the single strand. Sets of nonnatural nucleotide analogs, i.e. dideoxynucleotides, are incorporated into the media in which the polymerase is proceeding, and the analogs are selected so that when incorporated into the DNA molecule of the complementary strand, they terminate extension of the strand. Once the double-stranded DNA molecules are then denatured, the experimental vessel will then have in it a series of complementary nucleotide fragments each terminated by a dideoxynucleotide base. By then separating the nucleotides by length, usually by means of a gel electrophoresis technique, the length of the various fragments can be determined. If four of the experimental samples are processed at the same time, and each mixture normally includes a nucleotide analog for a different one of the four possible normal nucleotide base pairs, the four mixtures will each contain a set of fragments of differing lengths, and the relative position of each nucleotide within the original DNA fragment can be determined by comparative analysis of the lengths of the fragments from the four broths.

Thus to use the dideoxy nucleotide sequencing methodology, it is most appropriate to generate single-stranded DNA. However in most bacterial hosts, DNA normally exists in a double-stranded form, in circular fragments of DNA known as plasmids. Plasmids are double-stranded circles of DNA which can, if provided with a suitable origin of replication, replicate themselves when hosted in a cytoplasm of a suitable bacterial host. In many recombinant DNA procedures, the common intestinal bacteria E.coli is used as the appropriate host.

A variation on the dideoxynucleotide method of DNA sequencing makes use of the vector derived from the bacteriophage M13. The M13 phage vector is a single-stranded vector often used for sequencing. DNA of unknown sequence can be inserted into the M13 in its double-stranded form, i.e. replicating form, which replicates in host E.coli cells. The M13 phage genes then cause the E.coli cell to package single-stranded copies of the replicated DNA (the "+" strand) into phage particles which are secreted by the E.coli cells, which continue to grow. The single stranded DNA can readily be separated from the phage to isolate the large amounts of single-stranded DNA necessary for dideoxynucleotide sequencing. By utilizing oligonucleotide fragments as primers which hybridize to sites on the M13 vector adjacent to which unknown DNA has been inserted, and through elongation of the primers with polymerase, the unknown DNA can be efficiently sequenced through the use of the M13 phage vector. Utilizing this process, the single-stranded DNA will always be directionally uniform, that is to say the reading direction of the nucleotide sequence will always be from the hybridization site of the oligonucleotide primer through the unknown DNA in the same direction.

In efforts to sequence large segments of DNA, such as fragments of chromosomes or large genes, the orderly sequencing of small DNA fragments from one end to the other end of a large segment has, in the opinion of some, not proven to be the most efficient methodology for sequencing. Some scientists believe that it works out procedurally to be more practical to utilize random cutting of DNA fragments, and then to sequence large numbers of the random cuttings. The various sequence fragments thus determined can then be assembled by computer matching of the overlapping portions of the fragments. To ensure that all, or at least a very large portion, of the DNA in the large segment is accurately sequenced using this random fragment approach, a significant redundancy has to be built into the procedure. If the accuracy goal of a DNA sequencing process is such that, if a methodological end-to-end sequencing was done one would want to do it at least four times to get absolute accuracy, utilizing a purely random approach would require 22 fold over-sequencing of random DNA cuttings to provide a statistical likelihood of achieving the necessary sequencing of each individual base pair at least four times. Over-sequencing to this degree would obviously be an inefficient use of resources, if avoidable. It is therefore appropriate to search for techniques which allow the convenience of random sequencing of small fragments, and computer assembly the resulting fragments, while minimizing the amount of over-sequencing necessary to fill in all the gaps, and make sure that every single base pair is sequenced at least a certain number of times. To do this it would be extremely helpful if certain fragments could be sequenced in each direction. While it is possible to take each DNA fragment and make random inserts into the M13 phage vector, and then to isolate pairs of the M13 vectors which have the same insert in each of two opposite directions, this procedure is also relatively time consuming and laborious for use in mass DNA sequencing operations. Accordingly, a helpful procedure for automatically and easily changing the direction or orientation of DNA for DNA sequencing procedures.

SUMMARY OF THE INVENTION

The present invention is summarized in a DNA sequencing vector which includes first and second site specific recombination recognition sites which have located between them a vector unique restriction endonuclease cleavage site, there further being on the vector an initiation site for DNA replication which is located outside of the region between the first and second recombination recognition sites. The sites are oriented and arranged on the vector so that a site specific recombination event occurring between the first and second recombination recognition sites will reverse the orientation of any DNA between the recombination recognition sites, including the vector unique site and any DNA ligated therein, relative to the initiation site for DNA replication.

It is another object of the present invention to provide an M13 phage DNA sequencing vector which has incorporated into it provisions for inverting the direction of replication of a sequence fragment placed into the vector.

The present invention is also summarized in that a method of sequencing DNA includes the steps of randomly fragmenting a large segment of DNA into smaller fragments, inserting the fragments into copies of a DNA sequencing vector which has the capability to invert a specific portion of itself, creating and sequencing single-stranded DNA segments from a first orientation of the sequencing vector, exposing at least some of the random vectors to site specific recombination so as to inverse the orientation of the fragments in the vector and creating and sequencing DNA fragments of a second orientation from the subset of vectors.

It is an object of the present invention to provide an improved DNA sequencing vector which has the capability of readily reversing the orientation of a target DNA fragment placed within it.

It is another object of the present invention to couple such an invertible DNA sequence with a readily detectable marker such that colonies of bacteria harboring the vector which have incorporated in them a target DNA fragment can readily be detected by conveniently performed assay.

It is another object of the present invention to facilitate the mass sequencing of large segments of DNA by facilitating the process of analyzing the results of sequencing of random DNA fragments and assembling the fragments into whole sequences of larger DNA segments.

Other objects, advantages and features of the present invention will become apparent from the following specification when taken in conjunction with the accompanying drawings.

BRIEF DESCRIPTION OF THE DRAWINGS

FIG. 2A-2D is a complete listing of the Janus sequencing vector constructed in accordance with the present invention (SEQ ID NO. 1).

DESCRIPTION OF THE PREFERRED EMBODIMENT

In accordance with the present invention a DNA sequencing vector is created based on the standard M13 cloning vector which has been modified so that the DNA to be sequenced is inserted into the vector in such a way that the sequence may be conveniently reversed in orientation within the sequencing vector. The mechanism of this reversal is a site specific recombination event. This vector allows single stranded DNA to be created from the double-stranded DNA to be sequenced in either of the two possible orientations. Such a DNA sequencing vector with a reversible insert is particularly useful for large DNA sequencing operations in which redundant and repetitive sequencing of random DNA fragments is necessary to derive the sequence of a large segment of DNA. The reason for this usefulness is that the insert target DNA sequence can be readily flipped in direction, as needed, so that target DNA pieces can be readily created by primer extension from either end of a randomly cut inserted fragment of DNA.

The present invention envisions a double-stranded DNA vector, preferably a plasmid, into which a DNA fragment may be inserted for a DNA sequencing operation. Normally the DNA which used to be inserted into such a double-stranded DNA vector is, as yet, unsequenced. The DNA is inserted in the vector and then the vector is replicated and used to create single-stranded DNA for a DNA sequencing procedure. The preferred procedure is the DNA sequencing procedure based on dideoxynucleotide sequencing, a method well known to the prior art. Such a sequencing method, at least in the presently preferred techniques, is performed more conveniently with single-stranded DNA. The DNA fragment which is inserted into the sequencing vector so that it may be sequenced is generally referred to hereinafter as the target DNA sequence.

On a sequencing vector such as that described here, there is preferably a provision for the convenient and predictable insertion of fragments of target DNA. into the vector for sequencing. The most convenient method for this to be done is to provide a vector unique restriction endonuclease cleavage site at the locus where insertion of the target DNA is desired. This technique is common and well understood by those of ordinary skill in the art. It may also be desirable that more than one such restriction enzyme cleavage site be included at this locus in the vector.

On the DNA sequencing vector constructed in accordance with the present invention site specific DNA recombination recognition site sequences are placed flanking the site of insertion of the target DNA sequence into vector. Site specific recombination refers to a process by which an agent, typically an enzyme, catalyzes the recombination of DNA at two specific recognition sites. The agent enzymatically cuts the two strands at the two sites and recombines the severed end of each strand to the complementary severed end of the other strand. If the sites are located on two separate pieces of DNA, the two pieces may be joined by the process. If the two sites are on the same DNA molecule, as for example a plasmid, the recombinant event may create two plasmids or may reconfigure the orientation of parts of the plasmid, depending on the arrangement of the recognition sites. In the plasmid as described here, the site specific recombination recognition sites are oriented and arranged so that the DNA between them is flipped, or inverted in orientation, by the recombinant event. By placing the target DNA in a vector unique restriction enzyme site between the recombination recognition sites, the recombinant event will invert any inserted target DNA fragment as well.

The recombination recognition sites used in the subject vector are preferably the attachment sites for a protein known as lambda integrase. Lambda integrase is an enzyme encoded by the bacteriophage lambda that directs insertion of the native phage DNA into the chromosome of a bacteria infected by the bacteriophage, such as E.coli, by site specific recombination. The enzyme recognizes specific sites on both the phage, and on the bacterial chromosome, so that a site specific recombination, or integration, of the phage DNA into the E.coli chromosome is directed by the protein. The attachment site on the phage is known as attP, while the attachment site on the bacteria is referred to as attB. Although the attB site is actually in the genome of the bacteria rather than the phage, it is occasionally referred to as associated with the lambda phage. In the presence of the lambda integrase protein, the attachment site attB is split, as is the attachment site attP, creating complementary ends which are then welded together in a site specific recombination event. The new sites created by this recombinant event are referred to as attL and attR, represent the left and right borders of the inserted DNA sequence. All the steps of the integration reaction are coupled, in the sense that all four strands are cut, exchanged, and re-ligated without any stable intermediates appearing. The attP site and attB sites are unequal in size and complexity. The attP site is much larger and contains more binding sites to the enzyme. The minimal attB site is much smaller and may be reduced to a 15 base pair core. The identification of the sites and an analysis of the mechanism of this recombinant event may be found in Hsu, et al., *Nature*, 285, pp. 85–91 (1980).

While the lambda integrase recombinant system is described herein, with attP and attB as the recognition sites and lambda integrase as the recombination agent, other systems for site specific recombination may also be usable within the vector of the present invention. Other possible genetic recombination systems include those based on the hin (from Salmonella)-gin (from bacteriophage mu), flp (from the 2 micron circle of yeast), and the att80 system of phage Phi80. The requirement of such alternative systems is that the recombinant event be site specific and predictable, and that the recombinant agent be convenient.

Thus the sequencing vector of the present invention allows for either of two strands of a target DNA sequence to be selectively replicated in cells in culture. By insertion of the unknown target DNA sequence into the sequencing vector of the present invention, and in the absence of the lambda integrase protein, the sequencing vector will be efficient in creating single-stranded DNA of one of the two possible orientations of the inserted target DNA sequence. Primer directed generation of a complementary strand from adjacent the insertion then permits sequencing the inserted target DNA in one orientation. By then exposing the sequencing vector to the lambda integrase protein, either by in vitro chemical reaction or by transfection into an appropriate host capable of manufacturing the integrase protein, the site specific recombination event occurs, and the target DNA sequence is flipped in orientation within the vector. Then reverse primer extension under the same conditions as before would result in a complementary DNA to the opposite strand of the target DNA sequence and beginning at the opposite end. In this way, single-stranded DNA from either strand of the target DNA sequence can selectively and conveniently be created. The vectors having the inserted target DNA sequence in either orientation are stable, and can be stored or manipulated as desired. While this inversion feature of the vector makes the vector particularly suited for dideoxynucleotide sequencing, it is to be understood that other sequencing techniques are possible as well.

Another useful attribute of a sequencing vector is a marker gene to indicate the insertion of a target DNA fragment. Since the integration of target DNA into the vector will never occur with 100% probability, it is useful to have a marker so that after the ligation process has been initiated, vectors with inserted target DNA fragments can be segregated from those which failed to accept an insert. The test described here below is the beta galactosidase blue plaque test, commonly used with M13 vectors. The characteristic blue plaque characteristic of the M13 vector will be lost in vectors with inserted target DNA fragments, allowing convenient visual, i.e. colorometric, segregation of colonies harboring the inserts. The vector will retain the blue plaque test result, i.e. white, for either orientation of the invertible sequence.

One other useful attribute of this vector is that it is based on the commonly used M13 phage vector system. Since the sequencing procedure includes the step of primer initiated elongation of the alternate strand, it is an advantage that the Janus vector described here maintains the same M13 sequences adjacent the insert site for the target DNA. Thus, commercially available M13 primers may be used in the sequencing procedure for the Janus vector without alteration. It is important to consider the orientation of the primers and the sites they recognize, or bind to, in construction of the vector. It is most convenient if the primer binding sites are located outside of the recombination recognition sites, since then the primer binding sites will not invert. If the primer recognition site is between the recombination recognition sites, it too will be inverted in the recombination process and then a different primer site would have to be used to initiate primer extension in the inverted sequence.

The sequencing vector for use within the present invention has particular utility and procedures for the sequencing of large segments of DNA. In the current state of the art pragmatic techniques for sequencing such large segments of DNA, random cuts are made to resolve the larger DNA sequence into small fragments. The fragments are then placed into sequencing vectors, such as M13 phage vectors, to thus create a library of vectors harboring the fragments. Each of the vectors in the library is caused to replicate and secrete single-stranded DNA, and all the single-stranded DNA thus produced is sequenced. This creates, in essence, a random sequencing of a large number of fragments from the larger DNA segment. The sequences for the fragments are entered into a computer and the computer assembles the sequences of the fragments into the whole segment by matching up the overlaps and complements. By performing this procedure on a scale which is calculated to result in each portion of the DNA being sequenced at least a certain number of times, a high statistical probability of the repetitive sequencing of each base of the entire segment can be achieved. However, a purely random approach, by mathematical modeling, would appear to require at least twenty-two fold over sequencing to achieve the desired high probability that each strand has been sequenced in its entirety at least four times. The utilization of this vector in the manner described herein will allow the same standard to be achieved, that is to say a high probability that each strand has been sequenced in its entirety at least four times, with only a level of over sequencing needed in the range of six to eight fold. In this way the amount of effort involved in the random statistical sequencing of large DNA segments can be reduced and large DNA sequencing operations can be made more efficient through the use of a vector such as that described herein.

It should also be understood that the vector described herein could equally be useful in non-random sequencing. If a methodical end-to-end sequencing of a large DNA segment were performed, sequencing of the opposite strand or of the other ends of each smaller fragment, would still aid in increasing the confidence and lessening the error in the resulting sequencing procedures. Such sequencing of the opposite strand and of the other end of fragments is also facilitated by the vector described herein.

The present invention is illustrated with the Janus vector, the construction and use of which is described below. It is understood that this example is by way of illustration rather than limitation.

EXAMPLE

Construction of Janus Vector

The DNA sequencing vector with reversible insert site constructed in accordance with the present invention is referred to below as the Janus vector. It was constructed from the three components described as follows.

The first component was a M13 cloning vector. The particular vector utilized is referred to as the M13mp19. The entire nucleotide sequence of the M13mp18 phage cloning vector is given by Yanish-Perron, et al. *Gene,* 33, pages 103–119 (1985). The M13mp18 vector is an improved M13 phage cloning vector. The M13mp19 vector is simply the M13mp18 vector with the polylinker region (base pairs 6288 to 6231) reversed in orientation.

The second component needed for the construction of the Janus vector was the attP fragment derived from phage lambda DNA. This is the longer of the two recognition sites. The attP segment is that contained between base pairs numbers 27571 and 27972 in the sequence of the phage lambda, which was published in *Lambda II*, (Weisburg et al. Eds) Appendix 2, pages 519–576 (1983). The source of the lambda fragment actually utilized was plasmid pPH54 obtained from Dr. A. Landy of Brown University. Obviously, it could also have been synthesized from oligonucleotide segments. In the pPH54 fragment, the attP recognition site was altered to have a Hind III linker at base pair 27571, and was cut at the naturally occurring Bam HI site at base pair 27972. The attP fragment was then inserted into a Hind III/Bam HI fragment from plasmid vector pBR322.

A synthetic double-stranded DNA oligonucleotide was constructed to include the minimal attB sequence derived from *E.coli* and including a Sma I restriction site. This particular oligonucleotide was synthesized by a commercial DNA synthesis service, and the artificial Sma I site was included to provide a point of insertion for cloning target DNA into the vector to be constructed. Care was taken in the design of the oligonucleotide so that reading frame of the betagalactosidase complementing gene would be preserved and no stop codons would be introduced. Overhanging sticky ends were included to facilitate insertion into the vector. The sequence of the oligonucleotide was as follows:

```
Hind III overhang                                    Eco RI overhang
5'AGCTCCCGGGGTCAAGTTAGTATAAAAAAGCAGGCATGG (SEQ ID NO. 1,6649-6687)
    GGGCCCCAGTTCAATCATATTTTTTCGTCCGTACCTTAA5' (Complement of SEQ ID NO. 1,6653-6
```

To conveniently utilize the Janus construction, a pair of bacterial hosts were selected, one having and one not having the capability of conditioning the expression of the phage lambda integrase. The particular host used was JM101:sup, thi, delta(lac-proAB) [F', traD36, proAB, lacI⁹ZΔM25]. The second bacterial host utilized was JM101p(Int) which is the same *E.coli* JM101 carrying therein the plasmid pHS3-1, which was constructed by Gardner as described in *J. Bact.*, 172, pages 1529–1538 (1990). The plasmid pHS3-1 carries the lambda integrase gene driven by a hybrid Trp-Lac promoter referred to as Ptac. The resulting hybrid promoter is induced by iso-propyl-thio-galactoside (IPTG), so that the cell is competent to carry out site specific recombination by expression of the lambda integrase protein upon the induction by addition to the media of IPTG.

The actual construction of the vector began with a quantity of the double-stranded circular form of M13mp19 DNA. The plasmid DNA was digested to completion with the restriction endonucleases Hind III and Eco RI, and ligated with the synthetic attB fragment described above. The resulting ligated DNA fragment was transforemd into *E.coli* strain JM101 described above which is also commonly used host for M13 cloning vectors. The desired clone was the one with a replacement of the polylinker region (base pairs 6234–6284) of the M13mp19 vector with the synthetic oligonucleotide. The identification of the desired clone was confirmed by sequencing DNA of the plasmid through the inserted fragment. As expected from both the intended sequence, and from the observed sequence derived from the sequencing operation, the Eco RI and Sma I sites were present in the resulting plasmid, but the Hind III site was absent. The new construct, as intended, exhibited the blue plaque phenotype on indicator plates, proving that the alterations which had been made to the M13 vector did not interfere with the alpha complementary beta galactosidase test, which is a useful feature of commonly used M13 vectors This feature is one by which the successful introduction of a piece of target DNA into the Sma I site of the M13 vector for sequencing can readily be recognized by conversion of the sequencing vector from blue to white plaques in the colonies of *E.coli* harboring the vector on the indicator plates.

The insertion thus created may be readily understood by reference to the following sequence and the comparison of amino acid sequence from the resulting protein created both in the standard M13mp19 vector, and the Janus fragment.

DNA sequence of JANUS segment:

```
      /SmaI                         Att B              /EcoRI
ATGACCATGATTACGCCAAGCTCCCGGGGTCAAGTTAGTATAAAAAAGCAGGCATGGAATTCACTG
```

Double-stranded DNA at the intermediate vector thus created was then digested with a restriction endonuclease Ava II at a unique restriction site located in the M13mp19 DNA at position 5913, within the remnants of the Lac I gene. The Lac I gene is DNA which is non-essential to the functioning of the M13 vector, and which lies between the attB site introduced in the previous step and the plus and minus strand origins of replication of the M13 vector. The location of this insert is of importance since the objective of inverting the cloning site by recombination is to cause the opposite strand of the cloned insert to be incorporated into the single-strand form of the target DNA inserted in the altered vector created here. If the origin of single-strand DNA replication were to be included between the recombination sites along with the Sma I cloning site, the site of insertion of the target DNA fragment to be sequenced, it too would be inverted by the inversion process. If that was done, there would be no change in the sense of the strand created by single-stranded DNA replication by the sequencing vector.

E.coli DNA Polymerase I (large fragment) was then added to the linear DNA thus created to fill in the 5' overhangs resulting from the digestion. The object was to render the DNA molecule thus created flush ended. In a separate procedure, but in a similar manner, the attP fragment was excised from the plasmid pPH54 by digestion with the restriction enzymes Bam HI and Hind III, the fragment containing the attP fragment was isolated from the remainder of the plasmid, and the ends of the attP fragment were rendered flush by similar treatment with a DNA polymerase I. The flush ends of the two fragments thus created where then ligated together under conditions favoring flush end ligation. The following sequence illustrates the DNA sequences adjacent to the ligation thus created with the lower case letters indicating the bases filled in by the polymerase, and the capital letters indicating base pairs from the respective fragments.

```
M13mp19 ... G g a c ACGTTG (SEQ ID NO 1,5913-5922) ... attP ... G g a t c GACC ... M13mp19
            CCTG t g c a AC                                      CCTAG c t g G
                 /                                                     /
              flush joint                                          flush joint
```

The ligated DNA preparations were then transfected into E.coli, and candidate colonies were chosen and analyzed for the desired ligation product. The candidates were evaluated on the basis of the expected increase in the size of fragments resulting from restriction endonuclease digestion. The candidate plasmids were analyzed by restriction mapping, using several restriction enzymes, to identify one plasmid that had the attP segment inserted into the plasmid in the correct orientation for the desired inversion capability. The completed construction thus identified was referred to as the plasmid Janus.

The Janus plasmid vector described herein can be characterized in several ways. One increasingly common way by which DNA fragments are specified is referred to as DNAStar notation and is described in detail by Schroeder et al. Nucleic Acid Research 10:1, pages 69-84 (1982). In accordance with DNA.Star notation, the specification of the Janus vector plasmid can be characterized as follows:

Janus =
  M13mp19 (lend,5916) +
  "acgttg" +
  lambda (27571,27972) +
  "gatc" +
  M13mp19(5914,6233) +
  "agctcccggggtcaagttagtataaa
    aaagcaggcatgg" + (SEQ ID NO 1,6649-6687)
  M13mp19 (6285,rend)

The complete sequence of M13mp19 readily derived from the published sequence of M13mp18 sequence contained in Gene, 13, pages 103-119 (1985), referenced above, by understanding that the M13mp19 vector differs from the M13mp18 only by the inversion of the polylinker region contained between base pairs 6231 and 6288 of the published sequence. Thus by simply inverting those base pairs in the published sequence, the complete sequence of M13mp19 can readily be obtained.

Figure 1:
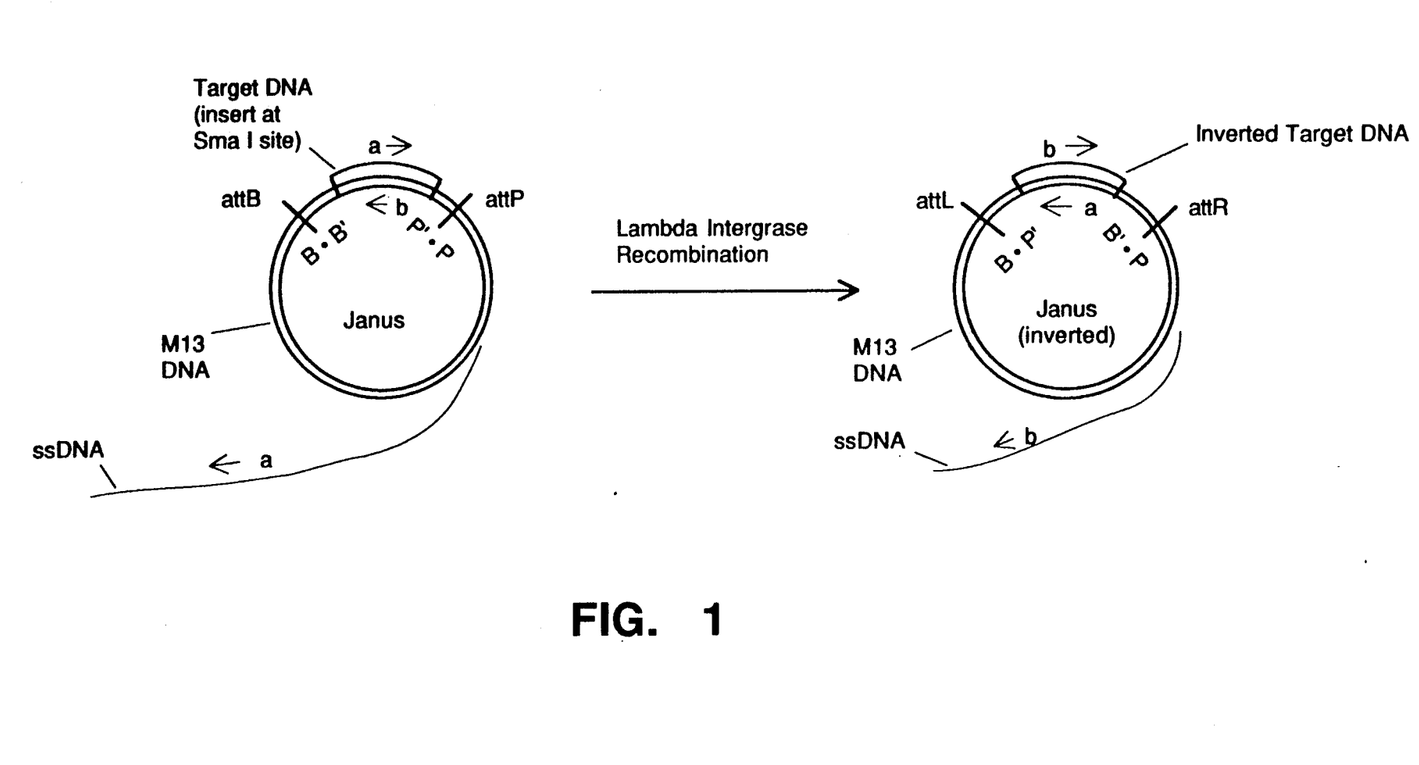
FIG. 1 is a schematic illustration of the vector constructed in accordance with the present invention illustrating the effect of the sequence inversion through a site specific recombination event.
Figure 2B:
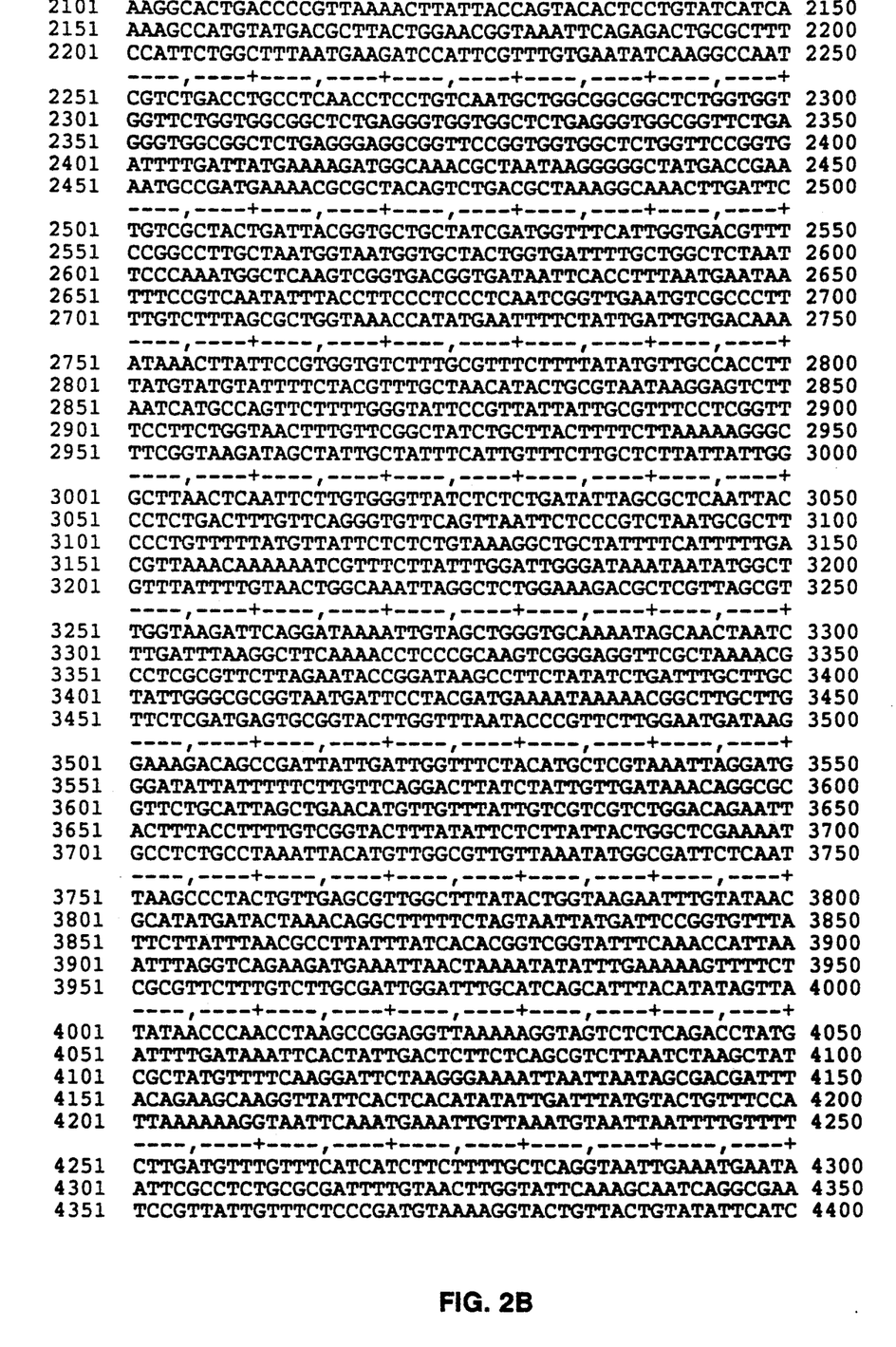
Figure 2D:
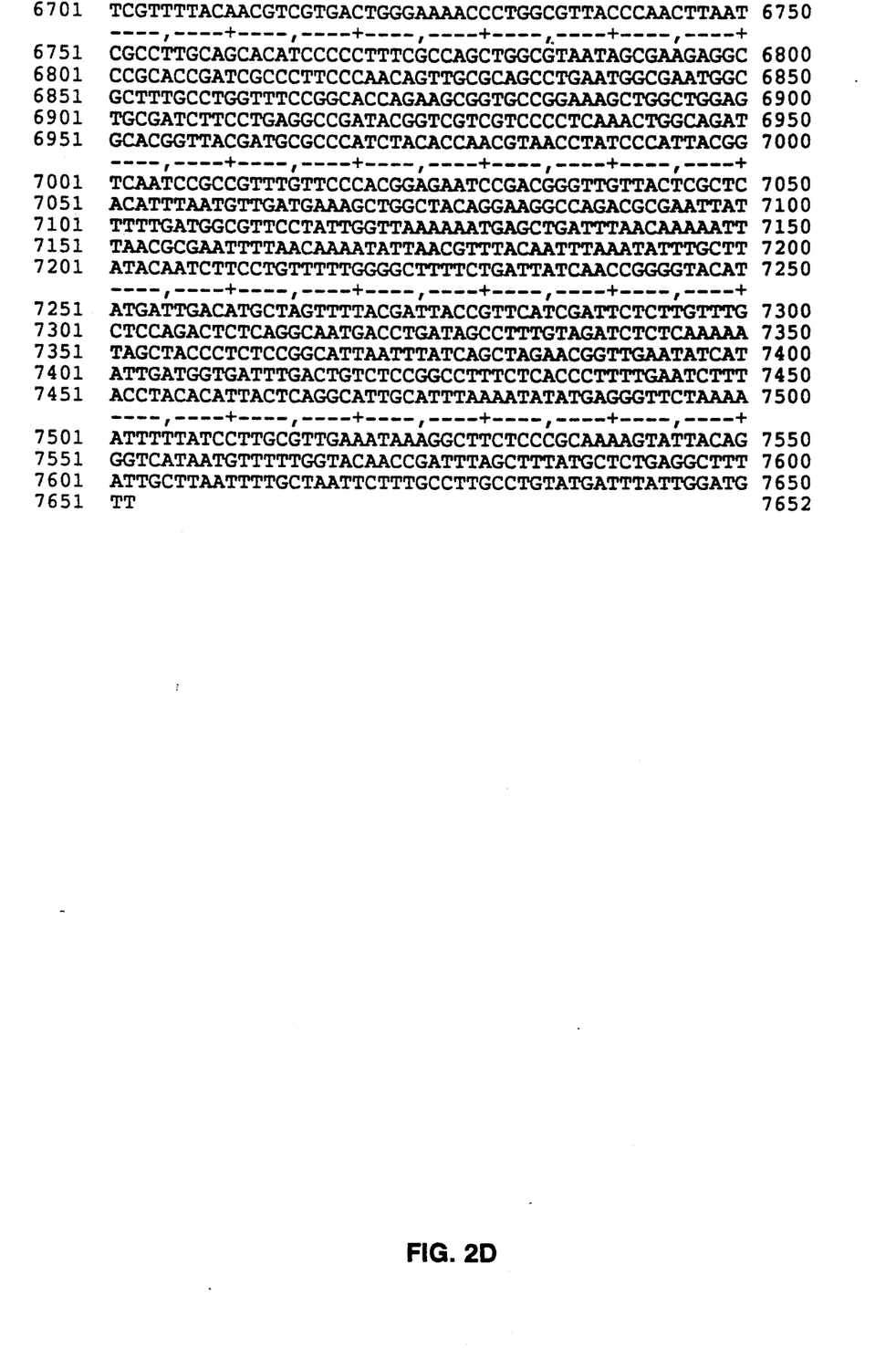

Submitted with this application as FIG. 2 is the complete DNA sequence of the 7,651 base pairs of the entire Janus vector. Referring specifically to the sequence, it may most readily be understood by considering the origin of the various segments which make up the entire vector. Base pairs 1 through 5913 are derived from the M13mp19 DNA vector, and are identical to base pairs 1 through 5913 of that vector. Base pairs 5914 through 5916 of the Janus vector are the filled in Ava II site from M13mp19. Base pairs 5917-5922 of the Janus vector are bases derived from the synthetic Hind III linker described above. Base pairs numbered 5923 through 6324 include therein the attP DNA from lambda phage, and contained at base pairs 27571 to 27972 of the lambda phage DNA sequence as referenced above. Within the Janus vector, base pairs 6325-6328 are the filled in Bam HI site from the lambda phage, while base pairs 6329 to 6333 are the filled in Ava II site from the cloning vector M13mp19. Base pairs 6332-6648 of the Janus vector are remaining DNA from the M13mp19 DNA, which correspond to base pairs 5917-6233 of that vector. Base pairs 6649 through 6687 of Janus are the synthetic Sma I site and synthesized attB sequence synthesized from oligonucleotides as described above. Base pairs 6688 through 7652 of the Janus vector are correspond to the remainder of the M13mp19 DNA sequence which sequence may be found at base pair 6285 to 7249 of the M13mp19 sequence referenced above.

The Janus vector thus created can be used similarly to other M13 cloning vectors to create single-stranded DNA. The vector has the complete capability to convert to the replicating phase, and to create single-stranded replicates thereof, which may be encapsulated and secrete from infected E.coli. Base pairs 5613-5716 or the Janus vector represent the origin of minus strand replication, while base pairs 5716 to 5825 represent the origins of plus strand replication of this phage vector.

The Janus phage vector thus created has the capability of actuating an inversion of a DNA segment contained within the vector in the form of a site specific integrase recombination of sites contained within the vector. The actual cross-over sites are contained at base pairs 6081-6087 in the attP site, and base pairs 6668-6674 in the attB site, which are seven base inverted repeats that form the actual cross-over site for lambda integrase mediated site specific recombination. Since these sites are placed in the vector in inverse orientation relative to each other, the initiation of lambda integrase recombination of a vector results in the complete inversion of the orientation of all the DNA placed between these sites in orientation within the vector. In other words, the exposure of the vector to the lambda integrase enzyme, under proper conditions for actuation of the enzyme, results in the complete reversal and orientation of all the DNA placed between base pairs 6087 and 6668 of the Janus vector described above. Between those base pairs is a Sma I cloning site (at base pairs 6655). The Sma I site is plasmid unique. Thus any DNA. incorporated into the Janus vector at the Sma I site will be located within the region which is inverted when the site specific recombination event occurs utilizing this vector.

To be most conveniently useful in a DNA. sequencing operation, a phage sequencing vector should include sequences for which there are readily commercially available primer oligonucleotides. Such primer oligonucleotides are DNA sequences intended to bind to the replicated single-stranded vector and which, in the presence of a suitable DNA polymerase, will initiate the transcription of single-stranded DNA from the primer along the single-stranded sequencing vector. It is an advantage of the Janus vector constructed in accordance with the present invention in that it allows the continued utilization of commercially available M13 oligonucleotide primers. Base pairs 6600-6623 of the Janus sequence contained herein is the sequence of a commercially available primer referred to as the "reverse primer," that can be utilized as a primer in a DNA sequencing operation utilizing the Janus clone. The use of such a termed reverse primer will initiate the polymerization of single-stranded DNA of an insert inserted into the Sma I site of the Janus vector after the recombination event of a insert clone derived from this vector.

Similarly, at base pairs 6713 to 6728 of the Janus vector is a sequence which is complimentary to the sequence of a commercially available primer, known as a "−40 primer" that an also be used to initiate single-stranded DNA polymerization on the template of the Janus vector. This primer can be used to initiate sequence elongation of inserts into the Janus vector before the recombination event triggered by the lambda integrase enzyme.

The position of the Sma I cloning site is that 6655, conveniently located between the two primers and also appropriately located between the two sites of the site specific integration events. There is an Eco RI site at 6687, but this is not suitable for sequence cloning because the DNA cloned into that site would not be inverted by the lambda integrase, since the site is outside of the cross-over site for the integrase mediated recombination process. Within the Janus nucleotide sequence, base pairs 6631 through 7125, represent the coding region for the alpha complementing region of beta galactosidase. The interruption by insertion of this coding region is responsible for the blue plaque test used to test for insertions into other M13 vectors. This test continues to work for the Janus vector as described herein through use of the exact same technique.

Confirmation of the site specific inversion was conducted by use of the Janus vector, as described above, without a DNA insert into the Sma I site therein. The vector was grown in E.coli strain JM101 p(Int) in the IPTG medium. The phage thus produced were assayed for the blue to white ratio on XG plates. Control samples were similarly grown in JM101 without p(Int). While the control samples propagat in JM101 gave rise to plaques which were 100% blue, the samples exposed to the integrase harboring plasmid were over 90% white. This result indicated that the segment between the core sequences of attP and attB had inverted in the JM101 p(Int) plaques. The inversion detached the lac z promoter in Janus from the gene for the Alpha complementing segment of beta galactosidase, thereby preventing blue plaque formation.

The inversion thus created was confirmed by sequencing DNA across the recombination junction of DNA recovered from one of the white plaques. The sequence was exactly as predicted reading from one-half of the attB into the other half of attP with the junction exactly at the expected position.

USE IN SEQUENCING

To meet a high level of accuracy in sequencing operations requires a certain level of redundant sequencing to obviate possibility of recurrent error. Current accuracy standards suggest that a high probability may be achieved when each strand has been sequenced at least four times, with at least one of the sequences being on each strand. To achieve a high degree of confidence that this level of over sequencing has been achieved by a purely random approach to shotgun cloning and sequencing would require 22 fold over sequencing, which is an excessive level of effort. Through the use of the Janus vector described herein, the same standard can be achieved with only six to eight fold-over sequencing using an initially random or shotgun approach to the sequencing operation.

To utilize the Janus vector in a cloning operation, from a 20 kilobase DNA insert, a random library can be created by sonication of the DNA to result in fragments of between 700 and 2300 base pairs in length. From such random fragments, 300 separate fragments are cloned into the Janus vector and can be cloned and replicated to create single-stranded DNA for sequencing. By sequencing all of the fragments contained in the 300 clones, approximately five-fold coverage of the entire 20,000 base pair segment can be statistically achieved. The sequences can then be assembled by computer. Both experience and computer simulation has indicated that at this level of over-sequencing a few gaps will still remain. To close those gaps and provide the desired level of redundant sequencing for each of the gaps, a subset of about 100 of the clones is selected for inversion. This subset is chosen from the 300 clones to include those clones which are adjacent to the remaining gaps, and to cover those regions which have been sequenced less than four times or regions which have been sequenced only on one strand, or sequences which have significant ambiguities in the consensus sequence so far obtained. These clones are then subjected to an inversion operation by exposing the plasmid clones to the lambda integrase protein. This can be done by in vitro exposure to integrase, or by removing the Janus vectors with the included sequences and then transfecting into integrase competent *E.coli* host (i.e. JM101 with pH53-1). The 100 clones thus selected will create single-stranded DNA for the selected 100 fragments, but each of the fragments will provide data from the opposite strand of the origin DNA and the sequences will begin at the opposite end of each fragment. Thus strong data is provided for the weak points left by the initial random screening approach. Three-fold additional sequencing from this covering set has been determined by computer model to provide more than an ample high probability of closing all the gaps in each strand, and then building up the minimum four fold redundancy at each point on the sequence. Since by this process seven to eight fold redundancy will have been achieved on average for each base sequence, the need to reach that primary data would be limited to a very few specific problem areas.

It must be understood that although all base pair sites, sequences and fragment lengths given here are believed accurate, occasional minor errors in base pair locations or sequences are possible given the present state of the art, without diluting the effectiveness or utility of the vector and the method described here.

It is also to be understood that the present invention is not limited to the particular embodiment disclosed herein, but embraces all such modified forms thereof as come within the scope of the following claims.

I claim:

1. A DNA sequencing vector comprising:
   a first site specific recombination recognition site;
   a second site specific recombination recognition site;
   a restriction endonuclease cleavage site located on the vector between the first and second recombination recognition sites;
   at least one primer recognition site for primer initiated DNA extension located on the vector; and
   an initiation site for single stranded DNA replication;
   the sites oriented and arranged on the vector so that a site specific recombination event occurring between the first and second recombination recognition sites will reverse the orientation of any DNA between the recombination recognition sites, including the restriction site and any DNA ligated therein, relative to the site for primer initiated DNA extension.

2. A DNA sequencing vector as claimed in claim 1 wherein the vector further comprises a marker gene coding for the expression of a product readily detectable by visual assay, the marker gene expression being altered by an insertion of target DNA at the restriction endonuclease cleavage sits so the colonies of bacteria hosting a target DNA insert can be visually screened to segregate insertion from non-insertion vectors.

3. A DNA sequencing vector as claimed in claim 2 wherein the marker gene is beta galactosidase.

4. A DNA sequencing vector as claimed in claim 1 wherein there are two of the primer recognition sites and wherein both of the primer recognition sites are located such that one and only one of the recombination sites is located between each primer recognition site and the endonuclease cleavage site.

5. A DNA sequencing vector as claimed in claim 1 wherein the recombination recognition sites are the attB and attP sites from the lambda phage.

6. A bacterial host harboring the vector of claim 1.

7. A DNA sequencing vector comprising:
   a first site specific recombination recognition site;
   a second site specific recombination recognition site;
   a restriction endonuclease cleavage site located on the vector between the first and second recombination recognition sites; and
   at least one primer recognition site for primer initiated DNA extension located on the vector wherein the primer recognition site sequence is found in the bacteriophage M13;
   the sites oriented and arranged on the vector so that the site specific recombination event occurring between the first and second recombination recognition sites will reverse the orientation of any DNA between the recombination recognition sites, including the restriction site and any DNA ligated therein, relative to the site for primer initiated DNA extension.

8. A DNA sequencing vector as claimed in claim 7 wherein the vector further comprises coding regions from the bacteriophage coding for the expression of gene products sufficient to encapsulate and secrete replicated DNA made from the vector.

9. A DNA sequencing vector comprising
   initiation sites for single stranded DNA replication from M13 phage;
   coding regions for M13 phage proteins sufficient to enable encapsulation and secretion of single stranded DNA made from the vector when hosted in a competent bacterial cell;
   a restriction enzyme cleavage site; and
   recognition sites attB and attP from the lambda phage positioned on the vector on opposite sides of the restriction enzyme cleavage site and between the cleavage site and the initiation sites for single stranded DNA replication, the recognition sites oriented on the vector so that exposure of the vector to the lambda phage integrase enzyme will catalyze a recombination of the vector between the attB and attP sites to reverse the orientation of the DNA between the sites relative to the remainder of the vector.

10. A DNA sequencing vector as claimed in claim 9 wherein the vector further comprises a marker gene coding for the expression of a product readily detectable by visual assay, the marker gene expression being altered by an insertion of target DNA in the restriction enzyme cleavage site so the colonies of bacteria hosting the insertions can be visually screened to segregate recombinant from non-insertion vectors.

11. A DNA sequencing vector as claimed in claim 10 wherein the marker gene is beta galactosidase.

12. A DNA sequencing vector as claimed in claim 9 wherein the restriction enzyme cleavage site is unique on the vector.

13. A DNA sequencing vector as claimed in claim 9 wherein the vector is the Janus vector.

14. A method of sequencing a segment of DNA comprising the steps of
(a) randomly fragmenting the segment of DNA into smaller fragments;
(b) inserting the fragments into copies of a DNA sequencing vector which has the capability to synthesize single stranded copies of itself and which has incorporated in it a pair of site specific recombination recognition sites, the fragments being inserted between the recombination recognition sites;
(c) creating single stranded DNA fragments of a first orientation from the sequencing vectors;
(d) sequencing the single stranded DNA fragments from step (c);
(e) exposing at least some of the vectors to a site specific recombination agent to effectuate recombination of the sequences of the vectors between the recombination recognition sites so as to reverse the orientation of the DNA between the sites relative to the remainder of the vectors;
(f) creating single stranded DNA fragments of a second orientation from the sequencing vectors from step (e); and
(g) sequencing the single stranded DNA fragments from step (f).

15. A method as claimed in claim 14 wherein in step (b) the fragments are inserted into a restriction enzyme cleavage site which is the only such site on the DNA sequencing vector.

16. A method as claimed in claim 14 wherein the vector in step (b) is phage vector including phage genes sufficient to enable encapsulation and secretion of replicated DNA in a suitable host, and wherein the creating step (c) is accomplished by (i) transfecting the vector into such a suitable host and culturing under conditions to favor the replication and secretion of phage containing the single stranded DNA and (ii) isolating the single stranded DNA from the phage.

17. A method as claimed in claim 14 wherein the vector in step (b) is phage vector including phage genes sufficient to enable encapsulation and secretion of replicated DNA in a suitable host, and wherein the creating step (f) is accomplished by (i) transfecting the vector into such a suitable host and culturing under conditions to favor the replication and secretion of phage containing the single stranded DNA and (ii) isolating the single stranded DNA from the phage.

18. A method as claimed in claimed 14 wherein the sequencing in steps (d) and (g) is performed by dideoxynucleotide sequencing.

19. A method as claimed in claim 14 wherein the vector includes as its recombination recognition sites the attP and attB sites of lambda phage, and wherein step (e) comprises exposing the vectors to lambda integrase enzyme to catalyze the site specific recombination event.

20. A method as claimed in claim 19 wherein the exposure of the vectors to the lambda integrase enzyme is done by transfecting the vectors into a bacterial host having lambda integrase enzyme therein.

21. A method as claimed in claim 19 wherein the exposure of the vectors to the lambda integrase enzyme is done by exposing the vectors to the lambda integrase enzyme in vitro.

22. A DNA sequencing vector comprising:
a first site specific recombination recognition site;
a second site specific recombination recognition site;
a restriction endonuclease cleavage site located on the vector between the first and second recombination recognition sites; and
an origin of single-stranded DNA replication located on the vector;
the sites oriented and arranged on the vector so that a site specific recombination event occurring between the first and second recombination recognition sites will reverse the orientation of any DNA between the recombination recognition sites, including the restriction site and any DNA ligated therein, relative to the origin of single-stranded DNA replication.

23. A DNA sequencing vector as claimed in claim 22 further comprising a marker gene coding for the expression of a product readily detectable by visual assay, the marker gene expression being altered by an insertion of any DNA into the restriction endonuclease cleavage site so that colonies of bacteria hosting the DNA sequencing vector can be visually screened to identify DNA insertion into the restriction endonuclease cleavage site.

24. A DNA sequencing vector as claimed in claim 23 wherein the marker gene is beta galactosidase.

25. A DNA sequencing vector as claimed in claim 23 wherein the origin of single stranded DNA replication is a sequence from the bacteriophage M13.

26. A DNA sequencing vector as claimed in claim 23 wherein the site specific recombination recognition sites are the attB and attP sites from the lambda phage.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 7652 base pairs
    ( B ) TYPE: nucleic acid
    ( C ) STRANDEDNESS: double
    ( D ) TOPOLOGY: circular ( i i ) MOLECULE TYPE: Other nucleic acid;
    ( A ) DESCRIPTION: synthetic recombinant plasmid ( i i i ) HYPOTHETICAL: no ( i v ) ANTI-SENSE: no ( x i ) SEQUENCE DESCRIPTION: SEQ ID NO:1:

```
AATGCTACTA CTATTAGTAG AATTGATGCC ACCTTTTCAG CTCGCGCCCC    50
AAATGAAAAT ATAGCTAAAC AGGTTATTGA CCATTTGCGA AATGTATCTA   100
ATGGTCAAAC TAAATCTACT CGTTCGCAGA ATTGGGAATC AACTGTTACA   150
TGGAATGAAA CTTCCAGACA CCGTACTTTA GTTGCATATT TAAAACATGT   200
TGAGCTACAG CACCAGATTC AGCAATTAAG CTCTAAGCCA TCCGCAAAAA   250
TGACCTCTTA TCAAAAGGAG CAATTAAAGG TACTCTCTAA TCCTGACCTG   300
TTGGAGTTTG CTTCCGGTCT GGTTCGCTTT GAAGCTCGAA TTAAAACGCG   350
ATATTTGAAG TCTTTCGGGC TTCCTCTTAA TCTTTTTGAT GCAATCCGCT   400
TTGCTTCTGA CTATAATAGT CAGGGTAAAG ACCTGATTTT TGATTTATGG   450
TCATTCTCGT TTTCTGAACT GTTTAAAGCA TTTGAGGGGG ATTCAATGAA   500
TATTTATGAC GATTCCGCAG TATTGGACGC TATCCAGTCT AAACATTTTA   550
CTATTACCCC CTCTGGCAAA ACTTCTTTTG CAAAAGCCTC TCGCTATTTT   600
GGTTTTTATC GTCGTCTGGT AAACGAGGGT TATGATAGTG TTGCTCTTAC   650
TATGCCTCGT AATTCCTTTT GGCGTTATGT ATCTGCATTA GTTGAATGTG   700
GTATTCCTAA ATCTCAACTG ATGAATCTTT CTACCTGTAA TAATGTTGTT   750
CCGTTAGTTC GTTTTATTAA CGTAGATTTT TCTTCCCAAC GTCCTGACTG   800
GTATAATGAG CCAGTTCTTA AAATCGCATA AGGTAATTCA CAATGATTAA   850
AGTTGAAATT AAACCATCTC AAGCCCAATT TACTACTCGT TCTGGTGTTC   900
TCGTCAGGGC AAGCCTTATT CACTGAATGA GCAGCTTTGT TACGTTGATT   950
TGGGTAATGA ATATCCGGTT CTTGTCAAGA TTACTCTTGA TGAAGGTCAG  1000
CCAGCCTATG CGCCTGGTCT GTACACCGTT CATCTGTCCT CTTTCAAAGT  1050
TGGTCAGTTC GGTTCCCTTA TGATTGACCG TCTGCGCCTC GTTCCGGCTA  1100
AGTAACATGG AGCAGGTCGC GGATTTCGAC ACAATTTATC AGGCGATGAT  1150
ACAAATCTCC GTTGTACTTT GTTTCGCGCT TGGTATAATC GCTGGGGGTC  1200
AAAGATGAGT GTTTTAGTGT ATTCTTTCGC CTCTTTCGTT TTAGGTTGGT  1250
GCCTTCGTAG TGGCATTACG TATTTTACCC GTTTAATGGA AACTTCCTCA  1300
TGAAAAAGTC TTTAGTCCTC AAAGCCTCTG TAGCCGTTGC TACCCTCGTT  1350
CCGATGCTGT CTTTCGCTGC TGAGGGTGAC GATCCCGCAA AAGCGGCCTT  1400
TAACTCCCTG CAAGCCTCAG CGACCGAATA TATCGGTTAT GCGTGGGCGA  1450
TGGTTGTTGT CATTGTCGGC GCAACTATCG GTATCAAGCT GTTTAAGAAA  1500
TTCACCTCGA AAGCAAGCTG ATAAACCGAT ACAATTAAAG GCTCCTTTTG  1550
GAGCCTTTTT TTTTGGAGAT TTTCAACGTG AAAAAATTAT TATTCGCAAT  1600
TCCTTTAGTT GTTCCTTTCT ATTCTCACTC CGCTGAAACT GTTGAAAGTT  1650
GTTTAGCAAA ACCCCATACA GAAAATTCAT TTACTAACGT CTGGAAAGAC  1700
GACAAAACTT TAGATCGTTA CGCTAACTAT GAGGGTTGTC TGTGGAATGC  1750
TACAGGCGTT GTAGTTTGTA CTGGTGACGA AACTCAGTGT TACGGTACAT  1800
GGGTTCCTAT TGGGCTTGCT ATCCCTGAAA ATGAGGGTGG TGGCTCTGAG  1850
```

-continued

```
GGTGGCGGTT CTGAGGGTGG CGGTTCTGAG GGTGGCGGTA CTAAACCTCC 1900
TGAGTACGGT GATACACCTA TTCCGGGCTA TACTTATATC AACCCTCTCG 1950
ACGGCACTTA TCCGCCTGGT ACTGAGCAAA ACCCCGCTAA TCCTAATCCT 2000
TCTCTTGAGG AGTCTCAGCC TCTTAATACT TTCATGTTTC AGAATAATAG 2050
GTTCCGAAAT AGGCAGGGGG CATTAACTGT TTATACGGGC ACTGTTACTC 2100
AAGGCACTGA CCCCGTTAAA ACTTATTACC AGTACACTCC TGTATCATCA 2150
AAAGCCATGT ATGACGCTTA CTGGAACGGT AAATTCAGAG ACTGCGCTTT 2200
CCATTCTGGC TTTAATGAAG ATCCATTCGT TTGTGAATAT CAAGGCCAAT 2250
CGTCTGACCT GCCTCAACCT CCTGTCAATG CTGGCGGCGG CTCTGGTGGT 2300
GGTTCTGGTG GCGGCTCTGA GGGTGGTGGC TCTGAGGGTG GCGGTTCTGA 2350
GGGTGGCGGC TCTGAGGGAG GCGGTTCCGG TGGTGGCTCT GGTTCCGGTG 2400
ATTTTGATTA TGAAAGATG GCAAACGCTA ATAAGGGGGC TATGACCGAA 2450
AATGCCGATG AAAACGCGCT ACAGTCTGAC GCTAAAGGCA AACTTGATTC 2500
TGTCGCTACT GATTACGGTG CTGCTATCGA TGGTTTCATT GGTGACGTTT 2550
CCGGCCTTGC TAATGGTAAT GGTGCTACTG GTGATTTTGC TGGCTCTAAT 2600
TCCCAAATGG CTCAAGTCGG TGACGGTGAT AATTCACCTT TAATGAATAA 2650
TTTCCGTCAA TATTTACCTT CCCTCCCTCA ATCGGTTGAA TGTCGCCCTT 2700
TTGTCTTTAG CGCTGGTAAA CCATATGAAT TTTCTATTGA TTGTGACAAA 2750
ATAAACTTAT TCCGTGGTGT CTTTGCGTTT CTTTTATATG TTGCCACCTT 2800
TATGTATGTA TTTTCTACGT TTGCTAACAT ACTGCGTAAT AAGGAGTCTT 2850
AATCATGCCA GTTCTTTTGG GTATTCCGTT ATTATTGCGT TTCCTCGGTT 2900
TCCTTCTGGT AACTTTGTTC GGCTATCTGC TTACTTTTCT TAAAAGGGC 2950
TTCGGTAAGA TAGCTATTGC TATTTCATTG TTTCTTGCTC TTATTATTGG 3000
GCTTAACTCA ATTCTTGTGG GTTATCTCTC TGATATTAGC GCTCAATTAC 3050
CCTCTGACTT TGTTCAGGGT GTTCAGTTAA TTCTCCCGTC TAATGCGCTT 3100
CCCTGTTTTT ATGTTATTCT CTCTGTAAAG GCTGCTATTT TCATTTTTGA 3150
CGTTAAACAA AAAATCGTTT CTTATTTGGA TTGGGATAAA TAATATGGCT 3200
GTTTATTTTG TAACTGGCAA ATTAGGCTCT GGAAAGACGC TCGTTAGCGT 3250
TGGTAAGATT CAGGATAAAA TTGTAGCTGG GTGCAAAATA GCAACTAATC 3300
TTGATTTAAG GCTTCAAAAC CTCCCGCAAG TCGGGAGGTT CGCTAAAACG 3350
CCTCGCGTTC TTAGAATACC GGATAAGCCT TCTATATCTG ATTTGCTTGC 3400
TATTGGGCGC GGTAATGATT CCTACGATGA AAATAAAAAC GGCTTGCTTG 3450
TTCTCGATGA GTGCGGTACT TGGTTTAATA CCCGTTCTTG GAATGATAAG 3500
GAAAGACAGC CGATTATTGA TTGGTTTCTA CATGCTCGTA AATTAGGATG 3550
GGATATTATT TTTCTTGTTC AGGACTTATC TATTGTTGAT AAACAGGCGC 3600
GTTCTGCATT AGCTGAACAT GTTGTTTATT GTCGTCGTCT GGACAGAATT 3650
ACTTTACCTT TTGTCGGTAC TTTATATTCT CTTATTACTG GCTCGAAAAT 3700
GCCTCTGCCT AAATTACATG TTGGCGTTGT TAAATATGGC GATTCTCAAT 3750
TAAGCCCTAC TGTTGAGCGT TGGCTTTATA CTGGTAAGAA TTTGTATAAC 3800
GCATATGATA CTAAACAGGC TTTTTCTAGT AATTATGATT CCGGTGTTTA 3850
TTCTTATTTA ACGCCTTATT TATCACACGG TCGGTATTTC AAACCATTAA 3900
ATTTAGGTCA GAAGATGAAA TTAACTAAAA TATATTTGAA AAAGTTTTCT 3950
CGCGTTCTTT GTCTTGCGAT TGGATTTGCA TCAGCATTTA CATATAGTTA 4000
TATAACCCAA CCTAAGCCGG AGGTTAAAAA GGTAGTCTCT CAGACCTATG 4050
ATTTTGATAA ATTCACTATT GACTCTTCTC AGCGTCTTAA TCTAAGCTAT 4100
CGCTATGTTT TCAAGGATTC TAAGGGAAAA TTAATTAATA GCGACGATTT 4150
ACAGAAGCAA GGTTATTCAC TCACATATAT TGATTTATGT ACTGTTTCCA 4200
TTAAAAAAGG TAATTCAAAT GAAATTGTTA AATGTAATTA ATTTTGTTTT 4250
CTTGATGTTT GTTTCATCAT CTTCTTTTGC TCAGGTAATT GAAATGAATA 4300
ATTCGCCTCT GCGCGATTTT GTAACTTGGT ATTCAAAGCA ATCAGGCGAA 4350
TCCGTTATTG TTTCTCCCGA TGTAAAAGGT ACTGTTACTG TATATTCATC 4400
TGACGTTAAA CCTGAAAATC TACGCAATTT CTTTATTTCT GTTTTACGTG 4450
CTAATAATTT TGATATGGTT GGTTCAATTC CTTCCATAAT TCAGAAGTAT 4500
AATCCAAACA ATCAGGATTA TATTGATGAA TTGCCATCAT CTGATAATCA 4550
GGAATATGAT GATAATTCCG CTCCTTCTGG TGGTTTCTTT GTTCCGCAAA 4600
ATGATAATGT TACTCAAACT TTTAAAATTA ATAACGTTCG GGCAAAGGAT 4650
TTAATACGAG TTGTCGAATT GTTTGTAAAG TCTAATACTT CTAAATCCTC 4700
AAATGTATTA TCTATTGACG GCTCTAATCT ATTAGTTGTT AGTGCACCTA 4750
AAGATATTTT AGATAACCTT CCTCAATTCC TTTCTACTGT TGATTTGCCA 4800
ACTGACCAGA TATTGATTGA GGGTTTGATA TTTGAGGTTA AGCAAGGTGA 4850
TGCTTTAGAT TTTTCATTTG CTGCTGGCTC TCAGCGTGGC ACTGTTGCAG 4900
GCGGTGTTAA TACTGACCGC CTCACCTCTG TTTTATCTTC TGCTGGTGGT 4950
TCGTTCGGTA TTTTTAATGG CGATGTTTTA GGGCTATCAG TTCGCGCATT 5000
AAAGACTAAT AGCCATTCAA AAATATTGTC TGTGCCACGT ATTCTTACGC 5050
TTTCAGGTCA GAAGGGTTCT ATCTCTGTTG GCCAGAATGT CCCTTTTATT 5100
ACTGGTCGTG TGACTGGTGA ATCTGCCAAT GTAAATAATC CATTTCAGAC 5150
GATTGAGCGT CAAAATGTAG GTATTTCCAT GAGCGTTTTT CCTGTTGCAA 5200
TGGCTGGCGG TAATATTGTT CTGGATATTA CCAGCAAGGC CGATAGTTTG 5250
AGTTCTTCTA CTCAGGCAAG TGATGTTATT ACTAATCAAA GAAGTATTGC 5300
TACAACGGTT AATTTGCGTG ATGGACAGAC TCTTTTACTC GGTGGCCTCA 5350
CTGATTATAA AAACACTTCT CAAGATTCTG GCGTACCGTT CCTGTCTAAA 5400
ATCCCTTTAA TCGGCCTCCT GTTTAGCTCC CGCTCTGATT CCAACGAGGA 5450
AAGCACGTTA TACGTGCTCG TCAAAGCAAC CATAGTACGC GCCCTGTAGC 5500
GGCGCATTAA GCGCGGCGGG TGTGGTGGTT ACGCGCAGCG TGACCGCTAC 5550
ACTTGCCAGC GCCCTAGCGC CCGCTCCTTT CGCTTTCTTC CCTTCCTTTC 5600
TCGCCACGTT CGCCGGCTTT CCCCGTCAAG CTCTAAATCG GGGGCTCCCT 5650
TTAGGGTTCC GATTTAGTGC TTTACGGCAC CTCGACCCCA AAAAACTTGA 5700
TTTGGGTGAT GGTTCACGTA GTGGGCCATC GCCCTGATAG ACGGTTTTC 5750
GCCCTTTGAC GTTGGAGTCC ACGTTCTTTA ATAGTGGACT CTTGTTCCAA 5800
ACTGGAACAA CACTCAACCC TATCTCGGGC TATTCTTTTG ATTTATAAGG 5850
GATTTTGCCG ATTTCGGAAC CACCATCAAA CAGGATTTTC GCCTGCTGGG 5900
GCAAACCAGC GTGGACACGT TGGCGCTAAT GCTCTGTTAC AGGTCACTAA 5950
```

-continued

```
TACCATCTAA  GTAGTTGATT  CATAGTGACT  GCATATGTTG  TGTTTTACAG  6000
TATTATGTAG  TCTGTTTTTT  ATGCAAAATC  TAATTTAATA  TATTGATATT  6050
TATATCATTT  TACGTTTCTC  GTTCAGCTTT  TTTATACTAA  GTTGGCATTA  6100
TAAAAAAGCA  TTGCTTATCA  ATTTGTTGCA  ACGAACAGGT  CACTATCAGT. 6150
CAAAATAAAA  TCATTATTTG  ATTTCAATTT  TGTCCCACTC  CCTGCCTCTG  6200
TCATCACGAT  ACTGTGATGC  CATGGTGTCC  GACTTATGCC  CGAGAAGATG  6250
TTGAGCAAAC  TTATCGCTTA  TCTGCTTCTC  ATAGAGTCTT  GCAGACAAAC  6300
TGCGCAACTC  GTGAAAGGTA  GGCGGATCGA  CCGCTTGCTG  CAACTCTCTC  6350
AGGGCCAGGC  GGTGAAGGGC  AATCAGCTGT  TGCCCGTCTC  ACTGGTGAAA  6400
AGAAAAACCA  CCCTGGCGCC  CAATACGCAA  ACCGCCTCTC  CCCGCGCGTT  6450
GGCCGATTCA  TTAATGCAGC  TGGCACGACA  GGTTTCCCGA  CTGGAAAGCG  6500
GGCAGTGAGC  GCAACGCAAT  TAATGTGAGT  TAGCTCACTC  ATTAGGCACC  6550
CCAGGCTTTA  CACTTTATGC  TTCCGGCTCG  TATGTTGTGT  GGAATTGTGA  6600
GCGGATAACA  ATTTCACACA  GGAAACAGCT  ATGACCATGA  TTACGCCAAG  6650
CTCCCGGGGT  CAAGTTAGTA  TAAAAAAGCA  GGCATGGAAT  TCACTGGCCG  6700
TCGTTTTACA  ACGTCGTGAC  TGGGAAAACC  CTGGCGTTAC  CCAACTTAAT  6750
CGCCTTGCAG  CACATCCCCC  TTTCGCCAGC  TGGCGTAATA  GCGAAGAGGC  6800
CCGCACCGAT  CGCCCTTCCC  AACAGTTGCG  CAGCCTGAAT  GGCGAATGGC  6850
GCTTTGCCTG  GTTTCCGGCA  CCAGAAGCGG  TGCCGGAAAG  CTGGCTGGAG  6900
TGCGATCTTC  CTGAGGCCGA  TACGGTCGTC  GTCCCCTCAA  ACTGGCAGAT  6950
GCACGGTTAC  GATGCGCCCA  TCTACACCAA  CGTAACCTAT  CCCATTACGG  7000
TCAATCCGCC  GTTTGTTCCC  ACGGAGAATC  CGACGGGTTG  TTACTCGCTC  7050
ACATTTAATG  TTGATGAAAG  CTGGCTACAG  GAAGGCCAGA  CGCGAATTAT  7100
TTTTGATGGC  GTTCCTATTG  GTTAAAAAAT  GAGCTGATTT  AACAAAAATT  7150
TAACGCGAAT  TTTAACAAAA  TATTAACGTT  TACAATTTAA  ATATTTGCTT  7200
ATACAATCTT  CCTGTTTTTG  GGGCTTTTCT  GATTATCAAC  CGGGGTACAT  7250
ATGATTGACA  TGCTAGTTTT  ACGATTACCG  TTCATCGATT  CTCTTGTTTG  7300
CTCCAGACTC  TCAGGCAATG  ACCTGATAGC  CTTTGTAGAT  CTCTCAAAAA  7350
TAGCTACCCT  CTCCGGCATT  AATTTATCAG  CTAGAACGGT  TGAATATCAT  7400
ATTGATGGTG  ATTTGACTGT  CTCCGGCCTT  TCTCACCCTT  TTGAATCTTT  7450
ACCTACACAT  TACTCAGGCA  TTGCATTTAA  AATATATGAG  GGTTCTAAAA  7500
ATTTTTATCC  TTGCGTTGAA  ATAAAGGCTT  CTCCCGCAAA  AGTATTACAG  7550
GGTCATAATG  TTTTTGGTAC  AACCGATTTA  GCTTTATGCT  CTGAGGCTTT  7600
ATTGCTTAAT  TTTGCTAATT  CTTTGCCTTG  CCTGTATGAT  TTATTGGATGTT 7652
```